(12) United States Patent
Ross et al.

(10) Patent No.: US 9,125,399 B2
(45) Date of Patent: *Sep. 8, 2015

(54) METHOD OF EMPLOYING ENHANCED PENETRATION OF WOOD PRESERVATIVES TO PROTECT WOOD AND A RELATED SOLUTION

(71) Applicant: KOP-COAT, INC., Pittsburgh, PA (US)

(72) Inventors: Alan S. Ross, Mt. Lebanon, PA (US); Kenneth Allen Cutler, Verona, PA (US)

(73) Assignee: Kop-Coat, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,915

(22) Filed: Oct. 15, 2013

(65) Prior Publication Data

US 2014/0039016 A1     Feb. 6, 2014

Related U.S. Application Data

(62) Division of application No. 13/079,905, filed on Apr. 5, 2011.

(51) Int. Cl.

| | |
|---|---|
| *A01N 25/00* | (2006.01) |
| *C09D 15/00* | (2006.01) |
| *A01N 25/02* | (2006.01) |
| *A01N 43/653* | (2006.01) |
| *B27K 3/02* | (2006.01) |

(Continued)

(52) U.S. Cl.
CPC ............... *A01N 25/00* (2013.01); *A01N 25/02* (2013.01); *A01N 43/653* (2013.01); *A01N 51/00* (2013.01); *A01N 53/00* (2013.01); *B27K 3/0285* (2013.01); *B27K 3/50* (2013.01); *B27K 3/52* (2013.01); *B27K 5/001* (2013.01); *C09D 15/00* (2013.01)

(58) Field of Classification Search
CPC ...................................................... A01N 27/00
USPC ........................................... 427/317; 514/644
See application file for complete search history.

(56) References Cited

U.S. PATENT DOCUMENTS

| | | | |
|---|---|---|---|
| 4,879,083 A | 11/1989 | Knudson et al. | |
| 4,950,685 A | 8/1990 | Ward | |

(Continued)

OTHER PUBLICATIONS

Lee, Myung Jac, "Adsorption of alkaline copper quat components in wood—mechanisms and influencing factors", Doctoral Thesis, University of Toronto, Department of Forestry, (online), Aug. 31, 2011, pp. 1-117.

*Primary Examiner* — Nathan T Leong
(74) *Attorney, Agent, or Firm* — Eckert Seamans Cherin & Mellott, LLC; Arnold B. Silverman

(57) ABSTRACT

A method of protecting wood through enhanced penetration of wood preservatives includes providing a solution including (a) at least one amine oxide, (b) at least one organic wood preservative and (c) a non-borate buffering based agent. The solution has a pH of 5 to 12.4 and preferably about 7 to 10. The solution is applied to the surface of the wood after which, with or without intervening storage, the materials are activated to effect enhanced penetration of the organic wood preservative into the wood. One may effect application at a solution temperature of about 30° C. to 75° C. and preferably about 50° C. to 60° C. to effect activation at a higher temperature and high relative humidity. In a preferred practice, the wood may be heated before and/or after application of the solution. The solution is also disclosed as a product.

22 Claims, 1 Drawing Sheet

(51) Int. Cl.
 *B27K 3/52* (2006.01)
 *B27K 5/00* (2006.01)
 *B27K 3/50* (2006.01)
 *A01N 51/00* (2006.01)
 *A01N 53/00* (2006.01)

(56) References Cited

U.S. PATENT DOCUMENTS

| | | |
|---|---|---|
| 5,468,284 A | 11/1995 | Sturm |
| 5,500,153 A | 3/1996 | Figueroa et al. |
| H1535 H | 6/1996 | Binder et al. |
| 5,763,338 A | 6/1998 | Sean |
| 5,833,741 A | 11/1998 | Walker |
| 5,846,305 A | 12/1998 | Payzant |
| 5,855,817 A | 1/1999 | Walker |
| 5,972,266 A | 10/1999 | Fookes et al. |
| 6,037,316 A | 3/2000 | Garner et al. |
| 6,235,403 B1 | 5/2001 | Vinden et al. |
| 6,274,199 B1 | 8/2001 | Preston et al. |
| 6,340,384 B1 | 1/2002 | Walker |
| 6,375,727 B1 | 4/2002 | Walker |
| 6,416,789 B1 | 7/2002 | Marks et al. |
| 6,448,279 B1 | 9/2002 | Tseng et al. |
| 6,485,790 B2 | 11/2002 | Walker et al. |
| 6,503,869 B1 | 1/2003 | Beste et al. |
| 6,508,305 B1 | 1/2003 | Brannon et al. |
| 6,508,869 B2 | 1/2003 | Tseng et al. |
| 6,527,981 B1 | 3/2003 | Tseng et al. |
| 6,572,788 B2 | 6/2003 | Walker |
| 6,582,732 B1 | 6/2003 | Bender et al. |
| 6,720,313 B1 | 4/2004 | Maynard |
| 6,811,731 B2 | 11/2004 | Archer et al. |
| 7,056,919 B2 | 6/2006 | Ross et al. |
| 7,655,281 B2 | 2/2010 | Ward et al. |
| 7,896,960 B2 * | 3/2011 | Ward et al. ............ 106/18.32 |
| 2002/0065206 A1 | 5/2002 | Tseng et al. |
| 2003/0077219 A1 | 4/2003 | Ploss et al. |
| 2003/0229170 A1 | 12/2003 | Biesecker |
| 2006/0078686 A1 | 4/2006 | Hodge et al. |
| 2009/0088481 A1 * | 4/2009 | Ward et al. ............ 514/644 |
| 2009/0156723 A1 * | 6/2009 | Durrant ............ 524/249 |
| 2009/0293761 A1 | 12/2009 | Richardson et al. |

\* cited by examiner

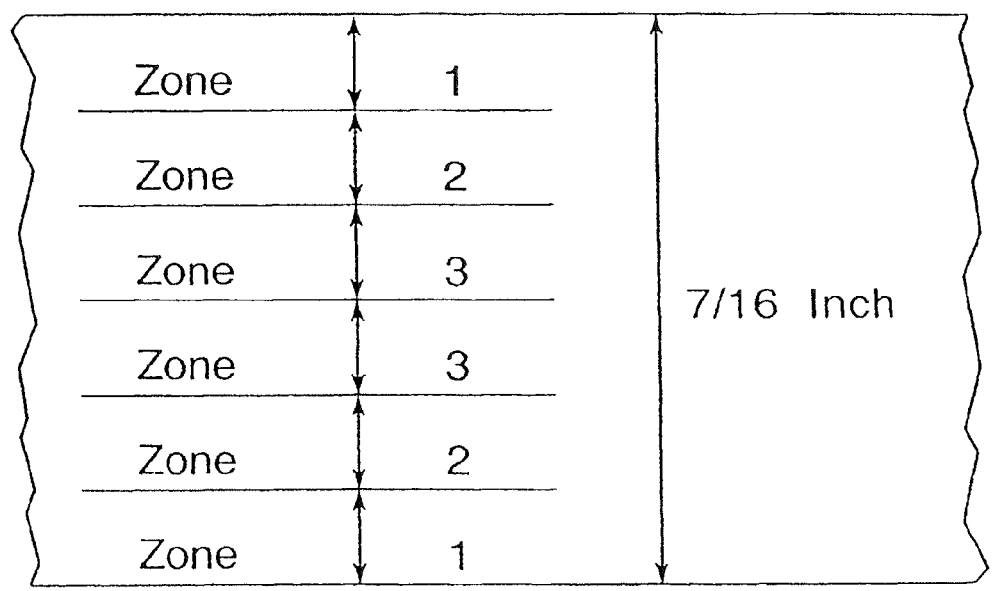

METHOD OF EMPLOYING ENHANCED PENETRATION OF WOOD PRESERVATIVES TO PROTECT WOOD AND A RELATED SOLUTION

BACKGROUND OF THE INVENTION

1. Field of the Invention

The present invention relates to an improved method of effecting enhanced penetration of wood preservatives into wood and, more specifically, it relates to such a method which employs a buffered compound which facilitates enhanced penetration of wood preservatives into the wood.

2. Description of the Prior Art

It has been known for many years to treat wood with materials which will protect the wood from deterioration. Among such approaches have been surface painting or the use of materials which will penetrate into the wood as by pressure impregnation or vacuum application. Among the materials used are fungicides, insecticides, decay-resisting materials, stain-resisting materials, weather proofing materials and others. See, for example, U.S. Pat. Nos. 4,879,083; 4,950,685; 5,468,284; 5,763,338; 5,833,741; 5,855,817; 5,972,266; 6,416,789 and 6,582,732.

In pressure and vacuum methods, the wood is treated with water or solvents that carry preservatives. The pressure or vacuum methods cause the wood to pick up large amounts of these carriers and, as a result, require kiln drying or oven drying or long-term air drying to allow the wood to be useful. Such drying of pressure or vacuum-treated wood using water as a carrier can cause structural defects such as warping, cracking and checking.

It has been known to suggest the use of amine oxides in combination with other materials in wood preservatives. See, for example, U.S. Pat. Nos. 6,274,199; 6,375,727; 6,448,279 and 6,527,981.

It has also been known to introduce into woods materials for fire-retardant properties. U.S. Pat. No. 6,811,731 discloses fire retardant protection achieved by treating green wood with a phosphate/borate.

It has also been known to suggest the combination of an amine oxide with a boron compound with the boron compound employed in a large enough amount to function as a preservative in wood. See U.S. Pat. No. 5,846,305; United States Published Patent Application No. 2002/0065206, now U.S. Pat. No. 6,508,869.

In the use of known prior art systems which required pressure impregnation or vacuum, capital investment for the equipment needed to achieve the desired pressure relationship influenced the economics of introduction of wood-preservative materials. Also, some prior art systems employed volatile solvents which presented environmentally undesirable conditions. In addition, such solvents added to the cost of such procedures. An example of such undesirable materials is petroleum distillates.

U.S. Pat. No. 7,655,281 discloses a method of protecting wood through enhanced penetration of wood preservatives by providing a solution which includes at least one amine oxide, at least one organic wood preservative, and a buffering agent. The buffering agent is selected from the group consisting of borates, boric acids, and combinations thereof.

There remains, therefore, a need for alternate means for effectively achieving the desired level of penetration of wood preservatives while having favorable economic aspects and avoiding risks to human health and environmentally-undesirable conditions.

SUMMARY OF THE INVENTION

The present invention has met the hereinbefore-described needs.

The method of the present invention permits enhanced penetration of wood preservatives through the use of solutions having a buffered pH above the pH of the wood achieved through the use of a combination of an amine oxide and a non-borate buffering agent.

In a preferred practice of the method, a solution is created with at least one amine oxide along with the wood preservative which is to be applied to the wood and a buffering agent. This solution has a pH of about 5 to 12.4 and preferably about 7 to 10 and most preferably about 7 to 8.5. It is applied to the surface of the wood. With or without intervening storage, activation results in the amine oxide and the buffering agent in the solution combining to enhance penetration into the wood of one or more wood preservatives. It is preferred that the application be at a solution temperature of about 30° C. to 75° C. and that the activation be at a higher temperature in a high relative humidity environment. The wood may also be heated before and/or after application of the solution to enhance penetration.

When a plurality of wood preservatives are employed, the depth of penetration of each may be to a different level, but, in general, would be enhanced as compared with introduction of the wood preservatives without the combination of the buffering agent and amine oxide present.

It is an object of the present invention to provide an improved method for enhancing depth of penetration into wood of wood preservatives.

It is another object of the present invention to provide such a method which does not require the use of pressure impregnation, vacuum systems or undesirable, volatile materials.

It is another object of the present invention to eliminate the redrying step required in prior art pressure and vacuum methods wherein water or a solvent carried the preservatives.

It is yet another object of the invention to provide such a method which can be employed on "green" lumber, i.e., lumber which contains undried sap or other green wood-based products in order to enhance penetration.

It is yet another object of the present invention to provide such a method wherein the wood to which the solution of the present invention has been applied may be stored for a significant period of time prior to a further activation stage.

It is a further object of the present invention to provide a solution for use in the method of the invention or a concentrate containing some or all of the desired compounds which can be diluted to create the desired solution with or without the addition of other compounds employable in the method.

It is yet another object of the present invention to provide such a method which effects rapid penetration of the wood preservatives into the wood.

It is another object of the invention to provide such a method which may involve heating at least one of (a) the wood prior to treatment, (b) the solution, and (c) the treated wood.

It is another object of the present invention to provide such a method which is usable on a wide variety of types of wood and resists undesired grain raising.

It is yet another object of the present invention to employ a non-borate based buffering agent in an amount effective for the desired buffering, but preferably not in the higher amount needed for the buffering agent to function as a preservative.

These and other objects of the invention will be more fully understood from the following description of the invention on reference to the illustration appended hereto.

BRIEF DESCRIPTION OF THE DRAWINGS

The FIGURE is a schematic illustration of a cross-section of a portion of a wood sample.

DESCRIPTION OF THE PREFERRED EMBODIMENTS

As employed herein, the terms "buffering agent" and "non-borate based buffering agent" mean buffers which have a combination of a weak acid, with a strong base or a strong base with a weak acid, or a weak acid and weak base and contains no substantial amount of borates, boric acid, or borax and shall expressly include, but not be limited to, buffers selected from the group consisting of citric acid/monopotassium citrate, ammonium/ammonia, potassium phosphate monobasic/potassium phosphate dibasic, monopotassium citrate/dipotassium citrate, monosodium ascorbate/disodium ascorbate, sodium bicarbonate/sodium carbonate, acetoxime/water, mononegative lysine/dinegative lysine, sodium phosphate monobasic/sodium phosphate dibasic, sodium phosphate dibasic/sodium phosphate tribasic, and potassium bicarbonate/potassium carbonate.

As employed herein, the term "wood-" means wood, wood-based materials, wood fiber materials, forest products, timber, lumber, engineered wood, millwork, joinery, wood laminates, laminated veneer lumber, plywood, laminated strand lumber, wood fiber composites, medium density fiberboard, particle board, hard board, oriented strand board, wood fiber resin composites, wood strand resin composites, wood particle resin composites and other wood and wood fiber-based materials and fabricated and semi-fabricated items made therefrom.

As employed herein, the term "wood preservatives" means organic compounds, halo-organic compounds, metalo-organic compounds, metallic salts and organo-salts, organo-phosphates and non-organoboron compounds having fungicidal, insecticidal, water-resistant, termite-resisting, decay-resisting, stain-resisting or other wood-protective properties.

As used herein, the term "amine oxide" or "amine oxide compound" refers to those compounds which are formed as reaction products in the reaction of tertiary amines and hydrogen peroxides and are represented by the general formula:

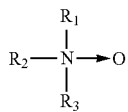

where $R_1$, $R_2$, and $R_3$ are independent and can be a linear, branched, cyclic, aromatic or any combination thereof of saturated or unsaturated $C_1$ to $C_{20}$ group and any $C_2$-$C_{20}$ carbon atom can be replaced with a hetero-atom selected from the group consisting of O, S and N.

Preferred amine oxides are alkyl dimethyl amine oxides such as decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide and octyl dimethyl amine oxide. Most preferred is N-alkyl ($C_{12}$-$C_{16}$)—N,N-dimethylamine oxide (ADO).

A buffering agent can be defined as an aqueous solution consisting of a mixture of a weak acid and its conjugate base or its weak base and conjugate acid. It has a property that the pH of the solution changes very little when a small amount of strong acid or strong base is added. Buffer solutions are used as a means of keeping pH at a nearly constant value in a wide range of chemical operations. In the present invention, the buffer helps to maintain a neutral-to-basic pH in the presence of the acids naturally present in the wood. As the pH of wood is typically around 5.4, the preferred buffering capacity should be above a pH of 5.4 in order to achieve maximum penetration. It will generally be about 5 to 12.4 and preferably about 7 to 10 and most preferably about 7 to 8.5, thereby putting it in the range to offset the inherent acidity in the wood. A dual buffering system generally consists of two different buffering agents, each with their own weak acid/conjugate base or weak base/conjugate acid or weak acid/weak base pairs, which combine to provide the desired pH.

In a preferred method of the present invention, a solution contains one or more amine oxides along with a buffering agent and at least one wood preservative with the solution having a pH of about 5 to 12.4 and preferably about 7 to 10 and most preferably about 7 to 8.5.

Below a pH of 7, the maximum penetration effectiveness is not achieved and above a pH of 10, the wood properties may be damaged. Natural woods have a pH in the acid range. For example, oak, Douglas fir, aspen and pine have pH's in the range of about 4.0 to 5.5.

A wide variety of amine oxides in the context of wood preservation have been known. See, for example, U.S. Pat. Nos. 6,343,084; 6,375,727; 6,416,789; 5,833,741; 6,527,981; 6,572,788; 6,508,869 and U.S. patent application Ser. No. 10/351,021, which became United States Published Patent Application Serial No. 20040248973, now U.S. Pat. No. 7,056,919, the disclosures of which are expressly incorporated herein by reference.

If desired, the materials may be provided in concentrate form in a solution of a suitable solvent, such as water, with the final solution to be applied being created by adding additional solvent and mixing the same in order to minimize shipping and storing of the solvent volume required to make up the difference between the concentrate solvent volume and the final solution solvent volume.

The solution preferably contains about 0.11 to 70 weight percent of one or more amine oxides and most preferably about 1 to 20 weight percent. The buffering agent is present in about 3 to 80 weight percent and preferably about 3 to 30 weight percent, all based on weight of total solution. The wood preservative is present in about 3 ppm to 50 weight percent based on weight of total solution and preferably about 20 ppm to 5,000 ppm. The solution is in water or another suitable solvent such as ethanol or ethylene glycol, for example.

The materials may be provided in the form of a concentrate which will be diluted prior to application to achieve the foregoing relationships.

The solution is applied to the wood by any desired means such as spraying, rolling on or dipping, for example. If desired, amounts of pressure or vacuum without totally filling the wood with liquid could be employed. The wood so treated may be stored for a period of time before activation or may be activated promptly thereafter by treatment at an elevated temperature in a high relative humidity environment. Application may be achieved at any temperature between ambient and boiling temperature, but in the preferred approach to the invention, the application will be achieved at a temperature of about 30° C. to 75° C. and preferably at a temperature of about 50° C. to 60° C. Activation is preferably achieved over a period of at least 8 hours at ambient temperature to steam temperature and preferably at about 70° C. to 95° C. and at a relative humidity of about 60 to 100% and preferably about 80 to 100%. It is preferred to preheat the wood to about 8° C. to 230° C. and most preferably at about 12° C. to 100° C.

It will be appreciated that more than one buffering agent, amine oxide or wood preservative may be employed and the ranges set forth herein refer to each category with a single compound or a combination of compounds.

The balance of the solution may be a suitable solvent such as water, ethanol or ethylene glycol, for example, or any desired additives such as water repellants, waxes, such as paraffin wax, for example, polymers, silicones and combinations thereof. A suitable wax-polymer emulsion is that sold under the trademark WRS-3 by Kop-Coat, Inc.

If desired, a suitable coloring agent such as an iron oxide pigment dispersion, red dye or phantom blue dye as offered under the trade designation Day Glo or others may be employed.

If desired, glycols and other additives which help solubilize materials such as the buffering agent, amine oxides, wood preservatives, water repellants and the like may be employed.

Also, additives such as glycols and alcohols which serve as solvents and may be employed in quantities of about 5 to 40 weight percent based on total solution. Among the suitable glycols are ethylene glycol, propylene glycol or polyethylene glycol.

The process of the present invention has been found to provide deeper and more rapid penetration than processes which do not employ such a solution. Enhanced performance may be achieved by applying heat to the wood before or after application or to the solution or by combinations thereof. The solution also may be applied without requiring prior art pressure impregnation or the use of vacuum conditions or undesirable, potentially health-hazardous and environmentally undesirable volatile solvents such as petroleum distillates.

Among the wood preservatives usable in the present invention are 3-iodo-2-propynyl butyl carbamate (IPBC), diiodomethyl-p-tolylsulfone (DIMPTS), halogenated organics, azoles, quaternary ammonium compounds, isothiazolones, metallic organics, borates, copper naphthenate, copper oxide, copper carbonate, tributyltin oxide, zinc omadine, salts of organics and metallorganics. The amount of these wood preservatives to be employed will be well known to those skilled in the art with the two additional compounds of the present invention expediting the rate of penetration into the wood. Within this group, insecticides such as synthetic pyrethroids, nicotinimides, organophosphates, phenylpyrazoles and others, for example, may be employed. Among the suitable insecticides are at least one material selected from the group consisting of nicotinimides, synthetic pyrethroids, borates and combinations thereof. Those skilled in the art will know the conventional quantities of the insecticides which may be employed.

Fungicides such as chlorothalonil, 2-(thiocyanomethylthio)benzothiazole (TCMTB), methylene bisthiocyanate, bethoxazins, DIMPTS (diiodomethyl-p-tolylsulfone), IPBC (3-iodo-2-propynyl butyl carbamate), triazoles, borates, isothiazalones, phenols, quaternary ammonium compounds and combinations thereof and others, for example, may be employed. Those skilled in the art will know well the conventional quantities of fungicides to be introduced into the wood.

It will be appreciated that when a plurality of wood preservatives are employed in the process of the present invention, different preservatives may penetrate to different depths of the wood than others. Also, depending upon the wood and its inherent wood pH and other characteristics of a specific wood and target penetration, it may be desirable within the range to modify the pH of the solution.

In another approach to the invention, the wood to which the solution has been applied may be stacked and penetration attained by wrapping the warm, freshly coated substrate stacks in an air-impervious material such as a suitable resinous plastic sheet and allowing it to stand at ambient temperature for 8 hours to three days. Additional penetration may be achieved thereafter through the activation process.

Another benefit of the present invention is that the wood surface appears to be clean and dry with no substantial undesirable grain raising.

The method of the present invention may be practiced in an in-line manner to process the wood efficiently while avoiding undesired forces such as would exist in pressurized treatment which may cause a straight board to depart from its desired straight configuration.

The wood may also be engineered wood or laminated wood having a glued layer or substantial amount of glue or resin therein with the method effecting penetration of the wood preservative through the glue or resin.

The method may be performed on wood with any amount of moisture content including green (wet) wood and on wood which has moisture at a level which does not exceed the fiber saturation point of the wood and on dry wood.

EXAMPLES

Various buffering systems were prepared by dissolving the appropriate reagents into one liter of deionized water. All buffering solutions were formulated to be between 0.5 molar and 1.0 molar in their final concentrations. Table 1 recites the composition of the buffering systems used in this study. A treating concentrate was prepared as outlined in Table 2. The buffering systems were then combined with the treating concentrate and deionized water to make 2 liters of treatment solution. The composition of each treatment solution is given in Table 3.

TABLE 1

CHEMICAL COMPOSITION OF BUFFER SYSTEMS

| ACIDIC COMPONENTS | | BASIC COMPONENTS | | |
| --- | --- | --- | --- | --- |
| AMOUNT | NAME | AMOUNT | NAME | BUFFER SYSTEM |
| 1.0 Mole | Citric Acid | 0.5 Mole | Potassium Hydroxide | Citric Acid/Monopotassium Citrate |
| 1.0 Mole | Ammonium Chloride | 1.0 Mole | Ammonium Hydroxide | Ammonium/Ammonia |
| 1.0 Mole | Potassium Phosphate Monobasic | 1.0 Mole | Potassium Phosphate Dibasic | Potassium Phosphate Monobasic/ Potassium Phosphate Dibasic |
| 1.0 Mole | Citric Acid | 1.5 Mole | Potassium Hydroxide | Monopotassium Citrate/ Dipotassium Citrate |

TABLE 1-continued

CHEMICAL COMPOSITION OF BUFFER SYSTEMS

| ACIDIC COMPONENTS | | BASIC COMPONENTS | | |
|---|---|---|---|---|
| AMOUNT | NAME | AMOUNT | NAME | BUFFER SYSTEM |
| 1.0 Mole | Ascorbic Acid | 1.5 Mole | Sodium Hydroxide | Monosodium Ascorbate/Disodium Ascorbate |
| 1.0 Mole | Sodium Bicarbonate | 1.0 Mole | Sodium Carbonate | Sodium Bicarbonate/Sodium Carbonate |
| 3.7 Mole | Boric Acid | 0.7 Mole | Borax | Standard Tru-Core |
| 1.0 Mole | Acetoxime | Excess | Water | Acetoxime/Water |
| 1.0 Mole | Lysine | 1.5 Mole | Sodium Hydroxide | Mononegative Lysine/Dinegative Lysine |
| 1.0 Mole | Sodium Phosphate Monobasic | 1.0 Mole | Sodium Phosphate Dibasic | Sodium Phosphate Monobasic/Sodium Phosphate Dibasic |
| 1.0 Mole | Potassium Bicarbonate | 1.0 Mole | Potassium Carbonate | Potassium Bicarbonate/Potassium Carbonate |
| 1.0 Mole | Ammonium | 1.0 Mole | Citrate | (Dual Buffer) Ammonium/Ammonia Citrate/Monosodium Citrate |

Finger-jointed, edge-glued, end-sealed Radiate pine boards (12"×5.4"×0.76") were treated with each treatment solution listed in Table 3 by dipping into the hot (60-65° C.) solution for one second. Boards were then wrapped under plastic for a 24-hour activation period.

The ingredients and molar relationships of each of the buffering systems are shown in Table 1. This buffering system is to be combined with the treating concentrate as set forth in Table 2. It will be noted that, in Table 2, the wood preservative and amine oxide are both provided. In this example, an amine oxide, which was coco-dimethylamine oxide, available under the trademark DELTA 2000, was present in the amount of 48.5%. The alkane diol is a glycol and functions as a "solvent." The TIMBERTREAT N-98 is a trademark for imidacloprid, which is an insecticide. TIMBERTREAT T is a trademark for tebuconazole, which is a fungicide. D-282 is an ultraviolet, optical brightener, which is a dye. TIMBERTREAT D is a trademark for an IPBC which functions as a fungicide. TIMBERTREAT ICP-5 is a trademark for permethrin, which functions as an insecticide. WOODTREAT 10 is a trademark for propiconazole, which functions as a fungicide.

TABLE 2

TREATING CONCENTRATE

| INGREDIENT | PERCENT BY WEIGHT |
|---|---|
| Alkane diol | 39.4 |
| Timbertreat N-98 (imidacloprid) | 0.5 |
| Timbertreat T (tebuconazole) | 0.4 |
| D-282 (UV optical brightener) | 0.1 |
| Timbertreat D (IPBC) | 6.2 |
| Timbertreat ICP-5 (permethrin) | 0.8 |
| Woodtreat 10 (propiconazole) | 4.1 |
| Delta 2000 (coco-dimethylamine oxide) | 48.5 |
| TOTAL | 100.0 |

Table 3 shows the composition of the treating solution with the buffer system identified in the left-hand column followed by the weight percent buffer (Table 1), the weight percent treating concentrate (Table 2), and the weight percent water.

TABLE 3

COMPOSITION OF TREATING SOLUTIONS

| BUFFER SYSTEM | WEIGHT PERCENT BUFFER | WEIGHT PERCENT TREATING CONCENTRATE | WEIGHT PERCENT WATER |
|---|---|---|---|
| Citric Acid/Monopotassium Citrate | 50 | 17 | 33 |
| Ammonium/Ammonia | 50 | 17 | 33 |
| Potassium Phosphate Monobasic/Potassium Phosphate Dibasic | 50 | 17 | 33 |
| Monopotassium Citrate/Dipotassium Citrate | 50 | 17 | 33 |
| Monosodium Ascorbate/Disodium Ascorbate | 50 | 17 | 33 |
| Sodium Bicarbonate/Sodium Carbonate | 50 | 17 | 33 |
| Sodium Borate/Boric Acid (Standard System) | 50 | 17 | 33 |
| No Buffer (Control System) | 0 | 17 | 83 |
| Acetoxime/Water | 50 | 17 | 33 |
| Mononegative Lysine/Dinegative Lysine | 50 | 17 | 33 |
| Sodium Phosphate Monobasic/Sodium Phosphate Dibasic | 50 | 17 | 33 |
| Potassium Bicarbonate/Potassium Carbonate | 50 | 17 | 33 |
| (Dual Buffer) Ammonium Citrate | 50 | 17 | 33 |

After the activation period, 1" thick cross sections were cut 4" from the sealed end of each board for measurement of penetration of active ingredients. Each cross section was then heated in an oven at 175° C. for ten minutes. After removal from the oven, a bromophenol blue indicator solution (0.4%) was applied to each cross sectional face.

The bromophenol blue indicator changes color from light green to dark blue in the presence of the amine oxides present in the treating solution. As a result, the degree of penetration of the amine oxides can be monitored by noting the depth of the dark blue color present in each cross sectional face.

After the bromophenol blue indicator had been present on the face of each cross sectional sample for five minutes, a marker was used to trace the depth of penetration of the amine oxide toward the center of each sample. A calibrated micrometer was then used to measure the distance between the edge of the sample and the marker space. The distances are indicated by zone numbers with zone 1 being the outermost zone, zone 2 being the next innermost zone, and zone 3 being the innermost zone. Penetration to the line between the two zone 3 regions would be regarded as 100% penetration. Two measurements (in inches) were made per side by determining the two deepest penetration points. Two separate measurements were used to assure that no one maximum would skew the results on a given sample of wood. Five samples of wood were measured for each treatment, and the results were then averaged. Since all samples had a cross-sectional thickness of 0.755 inch, full penetration to the center of the piece would be 0.378 inch.

TABLE 4

INITIAL BUFFER STUDY

| BUFFER SYSTEM | BUFFERED PH (TREATING SOLUTION) | AVERAGE PENETRATION IN. (PERCENT) |
|---|---|---|
| Citric Acid/Monopotassium Citrate | 3.3 | 0.199 (53%) |
| Ammonium/Ammonia | 8.3 | 0.227 (60%) |
| Potassium Phosphate Monobasic/Potassium Phosphate Dibasic | 7.0 | 0.218 (58%) |
| Monopotassium Citrate/Dipotassium Citrate | 4.9 | 0.195 (52%) |
| Monosodium Ascorbate/Disodium Ascorbate | 10.5 | 0 226 (60%) |
| Sodium Bicarbonate/Sodium Carbonate | 9.7 | 0.301 (80%) |
| Sodium Borate/Boric Acid (Standard System) | 7.6 | 0.330 (87%) |
| No Buffer (Control System) | N/A | 0.210 (56%) |

The results of the initial buffer study are presented in Table 4. Treating solutions having pH ranges of 3.3 (strongly acidic) to 10.5 (strongly basic) were evaluated. As expected, those systems having pH values of 7.0 and above (neutral to basic) achieved deeper penetration of the amine oxides compared to the control system (no buffer). Those buffer systems with pH values below 7.0 (acidic) failed to achieve penetration of the amine oxide compared to the control system (no buffer). It is noted that there is a significant correlation between the pH and choice of buffer with the average penetration expressed in inches and in percentages. For example, the citric acid/monopotassium citrate had a 3.3 pH, which is strongly acidic, penetrated 0.199 inch. The sample without buffer penetrated 0.210 inch. Considering as a standard system the sodium borate/boric acid at a pH of 7.6, which is slightly basic, the penetration was 0.330 inch or 87%. The sodium bicarbonate/sodium carbonate had a pH of 9.7, penetrated 80% or 0.301 inch, and the monosodium ascorbate/disodium ascorbate had a pH of 10.5 and penetrated 60% or 0.226 inch.

The results of a second series of tests are shown in Table 5. These tests employed the method described above and used only buffering systems which produced buffered treating solutions in the neutral to basic range. In this test, the sample without a buffer penetrated 44% or 0.167 inch, while the sodium borate/boric acid standard system had a pH of 7.7 and penetrated 0.288 inch or 76%. The acetoxime/water buffer had a pH of 7.7 and penetrated 65% or 0.247 inch, and the mononegative lysine/dinegative lysine had a pH of 10.5 and penetrated 60% or 0.227 inch. Potassium bicarbonate/potassium carbonate had a pH of 10.1 and penetrated 0.241 inch or 64%. These tests show that all of the buffering systems having a pH above 7.7 achieved better penetration into the wood than the control system which contains no buffer.

TABLE 5

SECOND BUFFER STUDY

| BUFFER SYSTEM | BUFFERED PH (TREATING SOLUTION) | AVERAGE PENETRATION IN. (PERCENT) |
|---|---|---|
| Acetoxime/Water | 7.7 | 0.247 (65%) |
| Mononegative Lysine/Dinegative Lysine | 10.5 | 0.227 (60%) |
| Sodium Phosphate Monobasic/Sodium Phosphate Dibasic | 6.8 | 0.197 (52%) |
| Potassium Bicarbonate/Potassium Carbonate | 10.1 | 0.241 (64%) |
| Sodium Borate/Boric Acid (Standard System) | 7.7 | 0.288 (76%) |
| No Buffer (Control System) | N/A | 0.167 (44%) |

A third series of tests were conducted employing the same methods as discussed above. The purpose of the third study was twofold—to expand the buffering systems in the basic pH range and to demonstrate the ability of some of the systems to achieve 100% penetration of the substrate. Basic buffering systems were prepared using the method described above. The dual buffer system, although not basic, was included in the study to evaluate its effectiveness. These were then combined with water and the treating concentrate in the ratios described in Table 3 and used to treat the Radiata Pine boards as described in the experimental method. In this third series, the main difference was that the activation period was increased from 24 hours to 120 hours. The results are shown in Table 6. It is noted that the sodium borate/boric acid standard system had a pH of 7.5 and a penetration of 94% or 0.0356 inch, while the no buffer control system had a penetration of 53% or 0.201 inch. The potassium bicarbonate/potassium carbonate had a pH of 10.3 and increased from 64% in penetration Table 5 to 69% of penetration in Table 6 suggesting that the increased activation period was beneficial to the result. Sodium phosphate dibasic/sodium phosphate tribasic had a pH of 10.0 and 80% penetration. Sodium phosphate monobasic monobasic/sodium phosphate dibasic had a pH of 8.1 and 93% penetration.

TABLE 6

THIRD BUFFER STUDY

| BUFFER SYSTEM | BUFFERED PH (TREATING SOLUTION) | AVERAGE PENETRATION IN. (PERCENT) |
|---|---|---|
| Monosodium Ascorbate/Disodium Ascorbate | 11.5 | 0.156 (41%) |
| Potassium Bicarbonate/Potassium Carbonate | 10.3 | 0.259 (69%)[1] |
| Sodium Phosphate Dibasic/Sodium Phosphate Tribasic | 10.0 | 0.302 (80%)[1] |
| Sodium Phosphate Monobasic/Sodium Phosphate Dibasic | 8.1 | 0.352 (93%)[2] |
| Sodium Borate/Boric Acid (Standard System) | 7.5 | 0.356 (94%)[2] |
| (Dual Buffer) Ammonium Citrate | 5.5 | 0.257 (68%) |
| No Buffer (Control System) | N/A | 0.201 (53%) |

[1]100% penetration was attained in 1 of 4 samples.
[2]100% penetration was attained in 3 of 4 samples.

It will be appreciated from the foregoing that the non-borate buffer systems of the present invention can be employed to achieve penetrations in excess of 60% and as high as 100%.

Whereas particular embodiments of the invention have been described herein, for purposes of illustration, it will be evident to those skilled in the art that numerous variations of the details may be made without departing from the invention as defined in the appended claims.

The invention claimed is:

1. A wood preservative solution comprising at least one amine oxide and at least one wood preservative and a non-borate dual buffering agent with the balance being at least one solvent, and
    selecting said buffering agent from the group consisting of
        (a) a mixture of a weak acid with its conjugate base and
        (b) a mixture of a weak base and its conjugate acid and contains no substantial amount of borates, boric acid or borax, said solution characterized by the property of having the interaction of the amine oxide with the non-borate dual buffering agent creating a synergistic effect to effect a greater depth of wood preservative penetration into the wood.

2. The solution of claim 1 including said non-borate dual buffering agent selected from the group consisting of citric acid/monopotassium citrate, ammonium/ammonia, potassium phosphate monobasic/potassium phosphate dibasic, monopotassium citrate/dipotassium citrate, monosodium ascorbate/disodium ascorbate, sodium bicarbonate/sodium carbonate, acetoxime/water, mononegative lysine/dinegative lysine, sodium phosphate monobisic/sodium phosphate dibasic, and potassium bicarbonate/potassium carbonate, and,
    employing water as said solvent.

3. The solution of claim 1 including said amine oxide being selected from the group of alkyl dimethyl amine oxides, decyl dimethyl amine oxide, lauryl dimethyl amine oxide, isoalkyl dimethyl amine oxide, myristyl dimethyl amine oxide, cetyl dimethyl amine oxide, stearyl dimethyl amine oxide, octyl dimethyl amine oxide and N-alkyl($C_{12}$-$C_{16}$)—N,N-dimethylamine oxide (ADO) and combinations thereof.

4. The solution of claim 1 including said solution having a pH of about 5 to 12.4.

5. The solution of claim 1 including employing said buffering agent in an amount of about 3 to 80 weight percent based on total solution weight.

6. The solution of claim 1 including employing said amine oxide in an amount of about 0.11 to 70 weight percent based on total solution weight.

7. The solution of claim 1 including employing said wood preservative in an amount of about 3 ppm to 50 weight percent based on total solution weight.

8. The solution of claim 1 including employing said buffering agent in a weight percent of about 3 to 30 percent based on total solution weight.

9. The solution of claim 1 including employing said amine oxide in a weight percent of about 1 to 20 percent based on total solution weight.

10. The solution of claim 1 including employing as said solution a solution having a pH of about 7 to 10.

11. The solution of claim 1 including employing at least one solvent additive in said solution.

12. The solution of claim 11 including said solvent additive selected from the group consisting of glycols, alcohols and combinations thereof.

13. The solution of claim 1 including said wood preservative being present in amount of about 20 ppm to 5000 ppm.

14. The solution of claim 1 including said wood being a wood selected from the group consisting of engineered wood and laminated wood having a glued layer or substantial amount of glue therein.

15. The solution of claim 1 including said wood preservative including at least one fungicide.

16. The solution of claim 15 including said fungicide selected from the group consisting of 3-iodo-2-propynyl butyl carbamate, diiodomethyl-p-tolylsulfone, triazoles, isothiazalones, phenols, quaternary ammonium compounds and combinations thereof.

17. The solution of claim 1 including said wood preservatives including at least one insecticide.

18. The solution of claim 17 including said insecticide including at least one material selected from the group consisting of nicotinimides, pyrethroids and combinations thereof.

19. The solution of claim 1 including a water repellent.

20. The solution of claim 19 including said water repellent including a wax-polymer emulsion.

21. The solution of claim 1 including said buffering agent being present in an amount that does not provide a substantial wood preservation effect.

22. The solution of claim 1 including said solution having a pH of about 7 to 8.5.

* * * * *

UNITED STATES PATENT AND TRADEMARK OFFICE
CERTIFICATE OF CORRECTION

| | | |
|---|---|---|
| PATENT NO. | : 9,125,399 B2 | Page 1 of 1 |
| APPLICATION NO. | : 14/053915 | |
| DATED | : September 8, 2015 | |
| INVENTOR(S) | : Alan S. Ross et al. | |

It is certified that error appears in the above-identified patent and that said Letters Patent is hereby corrected as shown below:

In the specification
Column 10, line 42, "monobasic monobasic" should read --monobasic--.
In the claims
Column 11, line 32, Claim 2, "monobisic" should read --monobasic--.

Signed and Sealed this
Nineteenth Day of April, 2016

Michelle K. Lee
*Director of the United States Patent and Trademark Office*